(12) United States Patent
Glowacz et al.

(10) Patent No.: US 10,670,737 B2
(45) Date of Patent: Jun. 2, 2020

(54) MOBILE TOF-PET INSERT

(71) Applicant: UNIWERSYTET JAGIELLONSKI, Cracow (PL)

(72) Inventors: Bartosz Glowacz, Zory (PL); Pawel Moskal, Czulowek (PL); Marcin Zielinski, Cracow (PL)

(73) Assignee: UNIWERSYTET JAGIELLONSKI, Kraków (PL)

( * ) Notice: Subject to any disclaimer, the term of this patent is extended or adjusted under 35 U.S.C. 154(b) by 403 days.

(21) Appl. No.: 15/742,897

(22) PCT Filed: Jul. 15, 2016

(86) PCT No.: PCT/PL2016/000082
§ 371 (c)(1),
(2) Date: Jan. 9, 2018

(87) PCT Pub. No.: WO2017/010896
PCT Pub. Date: Jan. 19, 2017

(65) Prior Publication Data
US 2018/0356536 A1 Dec. 13, 2018

(30) Foreign Application Priority Data
Jul. 16, 2015 (PL) ..................... P.413150

(51) Int. Cl.
*G01T 1/16* (2006.01)
*G01T 1/29* (2006.01)
*A61B 5/00* (2006.01)
*A61B 6/03* (2006.01)

(52) U.S. Cl.
CPC .......... *G01T 1/1603* (2013.01); *G01T 1/2985* (2013.01); *A61B 5/0035* (2013.01); *A61B 6/037* (2013.01)

(58) Field of Classification Search
CPC ..... A61B 5/0035; A61B 6/037; G01T 1/1603; G01T 1/2985
See application file for complete search history.

(56) References Cited

U.S. PATENT DOCUMENTS

2013/0284936 A1* 10/2013 McBroom ............ G01R 33/481
250/363.03

FOREIGN PATENT DOCUMENTS

WO WO-2015028598 A1 * 3/2015 .......... G01T 1/2985

* cited by examiner

*Primary Examiner* — Michael T Rozanski
(74) *Attorney, Agent, or Firm* — Mark M. Friedman

(57) ABSTRACT

A Time-of-Flight Positron Emission Tomography (TOF-PET) tomography insert. The insert includes detection modules and photoelectric converters. Each of the photoelectric converters is connected to an electronic signal processing circuit protected by a housing and comprising an electronic signal processing unit and a computer operable to control the electronic signal processing unit and to reconstruct and store images. Each of the detection modules further includes a liquid marker visible in a magnetic resonance image. The insert also includes a liquid marker device visible in the magnetic resonance image. Adjacent detection modules are detachably connected via coupling elements.

11 Claims, 7 Drawing Sheets

MOBILE TOF-PET INSERT

Figure 1:
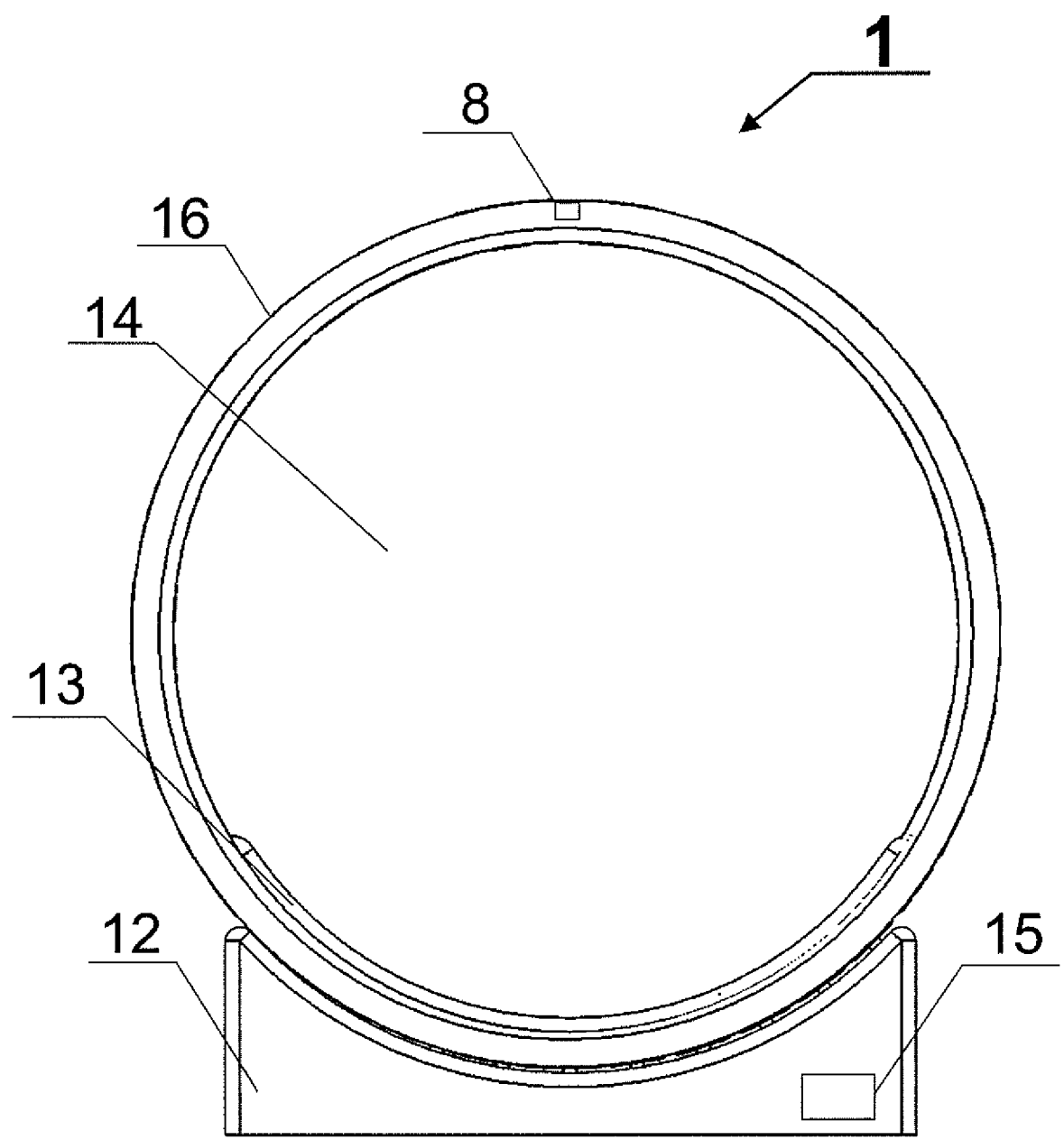

This application claims priority from PCT application No. PCT/PL2016/000082 filed Jul. 15, 2016 which claims priority from foreign application No. P.413150 filed Jul. 16, 2015, the disclosures of which are incorporated by reference.

The present invention relates to the mobile Time-of-Flight Positron Emission Tomography (TOF-PET) insert for the Magnetic Resonance Imaging (MRI) scanner which enables simultaneous imaging with PET and MRI techniques.

Access to anatomical and functional information of the body interior is possible using, for instance, various tomographic techniques which are based on the registration of radiation emitted from the area of tissues and processing collected data into anatomical image or information about the changes of physico-chemical properties occurring in studied area.

One of the techniques is Positron Emission Tomography (PET), which relies on the determination of the spatial distribution of chosen substance in the body and allows for tracking its concentration changes in time, thus allowing to determine the rate of metabolism of the individual tissue cells.

The selected substance is a radiopharmaceutical which is administered to the patient shortly before performing PET examination. The radiopharmaceutical, also called isotope label, is a chemical substance in which at least one atom is replaced by a radioactive isotope, for example: carbon, $^{11}C$, the oxygen $^{15}O$, nitrogen $^{13}N$, fluoride $^{18}F$, which is chosen to undergo a radioactive decay with emission of the positron (anti-electron). Positron is emitted from the nucleus of the isotope and penetrates into the tissue of the patient, where it annihilates with electron—present in the patient's body.

Annihilation process of the positron and electron, underlies the imaging PET technique, where the whole particles masses (electron and proton) are changed into energy, which is emitted as two annihilation photons, each with an energy of 511 keV. According to the momentum conservation principle the two photons propagate in opposite directions at an angle of 180 degrees in the rest frame of the positron and electron. The trajectories of the photons form a straight line which is called Line of Response (LOR). The stream of many annihilation photons generated in the described process is called a gamma radiation, and each photon is called the gamma quantum. The resulting gamma quanta are capable of penetrating matter—including the tissue of living organisms—which allows to detect them at certain distance from the patient. The process of annihilation of the positron and electron is usually within a few millimeters from the decay point of the radiolabel isotope. This fact constitutes a natural limitation of PET image accuracy at the level of a few millimeters.

The PET scanner includes devices that detect gamma radiation, electronics and software for specifying the location of the positron-electron annihilation position in the body, based on the information about the time and place of each of the two gamma quanta detection. Radiation detectors are commonly arranged in a form of single layer ring around the patient which consists of inorganic scintillator material. When the gamma quantum enters the scintillator material, it absorbs its energy, and then emits it in the form of light (photon flux). The mechanism of energy absorption of gamma rays by the scintillator may occur predominantly in two ways: through Compton or by photoelectric effects, however in the state of the art PET scanners for the purposes of calculation one takes into account only the photoelectric effect. Thus, it is assumed that the number of photons generated in the scintillator material is proportional to the energy of gamma quantum deposited in the scintillator. When two annihilation quanta will be registered by a pair of detectors within few nanosecond time interval, so-called coincidence window, one can locate the point of annihilation, lying on the line of the response LOR—which is the line connecting the center of detectors, or between points in scintillators stripe in which the gamma quanta deposited its energy. Coordinates of the annihilation point are obtained based on the time difference between the arrivals of gamma quanta to the detectors lying on the two ends of the LOR. In the literature, this technique is called the Time Of Flight (TOF) method, and PET scanners exploiting the signals time differences are called respectively TOF-PET scanners. To use this technique time resolving accuracy of several hundred picoseconds is required, for the scintillators detectors.

The state of the art PET scanners are large-size standalone devices. The cost of such device is very high, in the order of several million dollars.

To take full advantage of diagnostic information obtained with PET imaging technique, one should superimpose the map of the spatial distribution of the radiopharmaceutical administered to the patient, and the anatomical image of the investigated region of its body. Anatomical image can be obtained with other tomographic techniques such as Magnetic Resonance Imaging (MRI). The MRI tomography uses magnetic properties of atomic nuclei, in particular hydrogen atoms nuclei, composed of only one proton, widely occurring in matter, common in the tissues of living organisms, in a form of water molecule. The MRI technique allows to determine the density distribution of hydrogen atoms, which then is processed into morphological image of tissues.

Known MRI scanners are large size standalone devices, with the production cost in the order of several million dollars.

By superimposing the functional-PET, and morphological MR images one can significantly increase the diagnostic capabilities, as the PET image allows for precise determination of location and rate of metabolic changes, while at the same time the MR image allows to associate them with the individual organs. Thus nowadays, the PET and MR simultaneous imaging is intensively developed.

In the state of the art there are already known devices that combine the PET and the MRI scanners, so-called hybrid PET-MRI scanners. In the case of simultaneous operation of the two devices PET and MRI, it is necessary to overcome a number of technological obstacles. One of the problems is a strong constant magnetic field and strong electromagnetic pulses used in MRI, which disturb the operation of commonly used photomultiplier tubes and electronics for the processing of the signals registered by the PET detectors. In turn, the solutions currently used in PET systems may affect the uniformity of the local magnetic field, and disturb the operation of receiving coils which detects weak electromagnetic fields in the area of the examined tissue. This is due to the eddy currents and electromagnetic waves induced in the electronic circuits of PET scanner.

From the US patent document US 20060052685 A1, a solution is known based on a system of two independent and spatially separated PET and MRI devices, between which patient is displaced on a movable bed, common for both modalities. Although such an arrangement avoids the problem of mutual interference between the two systems, it does not ensure the simultaneity of both functional and anatomical imaging, and also is not performed in the same place. This creates a high risk of displacement of one image with respect to the other. Images of organs of the abdominal cavity are the most vulnerable to the artefacts, as the organs may move and change their shape, as a result of experienced acceleration during patient transport between scanners or, as previously mentioned, physiological movements.

A similar solution, in which the PET and MRI scanners are spatially separated and positioned in close proximity to each other, is reported in U.S. Pat. No. 8,013,607.

U.S. Patent Application No. 20130006091 A1, reveals an invention in which the PET detector is located directly outside the tunnel of MRI scanner, configured in a way to permit the change of its geometry size to be adjusted to the size of imaged object and provide undisturbed movement of the patient into the bore of the MRI scanner. In this method, the object is firstly subjected to the MR scan and later the PET imaging is performed, which requires to displace the diagnosed object into the field of view of the PET detector, located outside the tunnel of MRI scanner. Described method reduces the probability of image artifacts occurrence associated with the movement of the investigated object, only to a certain extent. Another problem is the time required for the object to be moved between two systems, folding and unfolding the PET detector, as well as the repeatability of this operation, which may influence the geometric relations between the detection modules, and thus the image reconstruction. It is also important, what was reported in the cited patent application, that for MR imaging the transceiver coil designed for the whole body has to be used. This coil surrounds the MRI scanner tunnel. In the MRI technique, it is common to use coils for imaging of specific areas of the body, so the investigated object fills as much as possible the volume limited by the coil construction. One describes this property by so-called filling factor parameter, which value determines the strength of the resonant signal which may be detected from the object inside the coil. The use of the whole-body coil for the head imaging substantially limits the amplitude of the recorded resonant signal, because of the large disparity between the volume enclosed by the coil and the MRI cylinder diameter (typically 60-70 cm), and the volume of the head (diameter typically 15-20 cm). For example, a typical transceiver coil dedicated to study head has about 26 cm internal diameter. The signal recorded by a resonant coil, adapted for whole body imaging, may then be 5 to 10 times weaker than that recorded using a head coil (coils for imaging the head) assuming the same volume of the test object.

In the present state of technique, as described in U.S. Patent No. 20070102641 A1, the PET detector is also known, arranged along the tunnel of MRI scanner. Indeed, this solution allows simultaneous recording of images with the two methods. However the PET detector, covers only about 25 cm long cylindrical volume in which the patient is placed. Because of this fact it is inevitable to move the patient, but this time within one device, at the time of imaging of the whole body or its larger parts. Typically, the patient is moved by a distance equal to a half the width of the PET detector ring, so that recorded images can be then combined together relying on the repetitive parts of subsequent acquisitions. The patient 180 cm tall requires, therefore, about 17 independent PET scans between which his body is being moved together with the scanner bed. Superimposing images increases the systematic uncertainty during the reconstruction process. In addition, a significant drawback is a decrease with time in the activity of a radioisotope administered to the patient, which in consequence forces correction to the computed data recorded in the later time of the imaging process.

From the Polish patent application no. P. 405184, a hybrid TOF-PET/MRI tomograph is known, comprising a TOF-PET and MRI tomographs, characterized in that the TOF-PET tomograph comprises a plastic scintillator bars arranged circumferentially inside the working magnetic field of a transceiver coil of the MRI scanner, and photo-electric converters of light signals from the scintillator stripes to electrical signals, and the photoelectric converters are outside the working area of the magnetic field of the MRI scanner. In the described solution the embodiment of the hybrid TOP-PET/MRI tomograph, allows simultaneous PET and MR imaging, but does not allow to use for this imaging systems which are used in the traditional MR. The second obstacle and limitation of this technology is the placement of photoelectric converters outside the working area of the MRI magnetic field. This requires the use of long stripes of plastic scintillator elements or optical fibers which allow to guide the light signal out of the MRI magnetic field area. Longer optical path to the photoelectric converters limits the flux of light reaching these converters. Presented solution can be used only in the production of new hybrid TOF-MRI scanners. However it cannot be applied to existing MRI devices.

Presently used PET-MRI hybrid tomographs are bulky standalone devices, production cost of which is very high.

The obtained hybrid PET/MRI images may be used in research on the physiological processes where it is essential to accurately associate the appropriate changes in the tissue with the metabolism of a radiopharmaceutical at the time of imaging.

The U.S. Pat. No. 7,218,112 presents solution with the use of silicon photomultipliers. The described method enables simultaneous imaging in the relatively large transverse field of view. In this solution, PET detectors are between the transmitting-receiving coils surrounding the patient and gradient coils. The PET detectors are composed of lutetium oxyortosilicon crystals (LSO), connected optically to the matrix of avalanche photodiodes, with integrated cooling system and the analog readout electronics. Detection modules are enclosed in copper shields. However, such placement of PET tomograph in the tunnel of MRI scanner, can lead to the disturbances of magnetic fields, and electromagnetic signals used in MRI, and distortion of signals of PET tomograph. The main factors causing the described disruptions are: converters, electronic circuits, cooling systems, which are placed between embodiment of the transmitting-receiving coil and the gradient coil, the transmission of electric signals between PET detectors and the transmitting-receiving coils and gradient coil, scattering of annihilation quantum in the MRI transmitting-receiving coils, which are placed between the patient and the PET detector layer.

However, in the case of hybrid systems, still unsolved the problem remains of use of the coils designed to examine specific parts of the body, e.g. head or limb. Use of the head coil is technically possible, but the construction elements of such coil made of plastic and metal conductors, are placed on the way of the gamma quantum flight path to the PET detectors, originating from the annihilation of the positron and electron in the examined volume. This fact limits the field of view of the PET detectors (so-called acceptance), and in addition can cause gamma quantum scattering, thus negatively affect spatial resolving power of PET imaging.

Therefore, it would be favorable to construct a device for imaging using low-cost plastic scintillators, which would allow simultaneous recording of gamma radiation and magnetic resonance imaging with a wide field of view, giving the ability to eliminate artifacts which may distort the picture due to the movement of the object, and the systematic uncertainties, that arise in the process of superimposing the images taken in different places and at different times. This would allow for an effective functional and morphological imaging at the same time.

The subject of present invention is to provide a TOF-PET insert, which will be a TOF device for imaging with PET technology, which can be placed inside any transceiver coil of existing MRI scanners, and after placement of such insert inside the transceiver coil of the MRI scanner, it would be possible to make simultaneous TOF-PET and MRI imaging, without interrupting the operation of TOF-PET and MRI scanners. The mechanical construction of the TOF-PET insert should make possible adjusting the size of the insert to the dimensions and shape of various types of existing transmitting-receiving coils of existing MRI scanners, both which are permanently built-in to the MRI scanner enclosure, and local coils dedicated to perform studies of individual parts of the patient body.

A TOF-PET tomography insert, according to the invention, is comprised of detection modules, each detection module comprising a scintillator stripe connected, at each end, to a photoelectric converter to convert light signals from the scintillator stripe to electric signals, and further connected to an electronic signal processing circuit protected by a housing, equipped with an electronic signal processing unit and with a computer having a software for steering the electronic signal processing unit, and a software for reconstruction and preserving the image, and is characterised in that the detection modules are made entirely of non-magnetic material, and that each detection module is equipped, at each end, with a liquid marker, wherein the tomography TOF-PET insert is equipped with a liquid marker device, and each detection module is equipped with coupling elements for detachable connection of adjacent detection modules. It is preferable, when the coupling element constitutes a protrusion, that is located on a cover of a single detection module, and a groove placed on an adjacent detection module.

It is preferable, when TOF-PET tomography insert has a protective layer, made of non-magnetic material to protect the detection modules from inside of a working space formed by the detection modules, after coupling thereof.

It is preferable, when the photoelectric converters are silicon photomultipliers arranged in a two-dimensional matrix, having at least two elements.

It is preferable, when the liquid marker device is located on the front face of the tomography insert, perpendicular to the scintillator stripes.

It is preferable, when the liquid marker device constitutes an ampoule with an aqueous solution of a chemical compound, shortening the longitudinal relaxation time of water.

It is preferable, when the liquid markers placed at the ends of the detection modules, have the form of ampoules with an aqueous solution of a chemical compound, shortening the longitudinal relaxation time of water.

It is preferable, when the TOF-PET tomography insert has a triggering unit.

It is preferable, when the TOF-PET tomography insert is equipped with at least one bracket.

It is preferable, when the bracket is equipped with an output slot for the electronic signal processing circuit, placed at the end of each detection module.

It is preferable, when the TOF-PET tomography insert is equipped with a support base made of non-magnetic material.

It is preferable, when the TOF-PET tomography insert is equipped with a bracket and a support base, in such a way that the bracket is attached to the support base.

Figure 2:
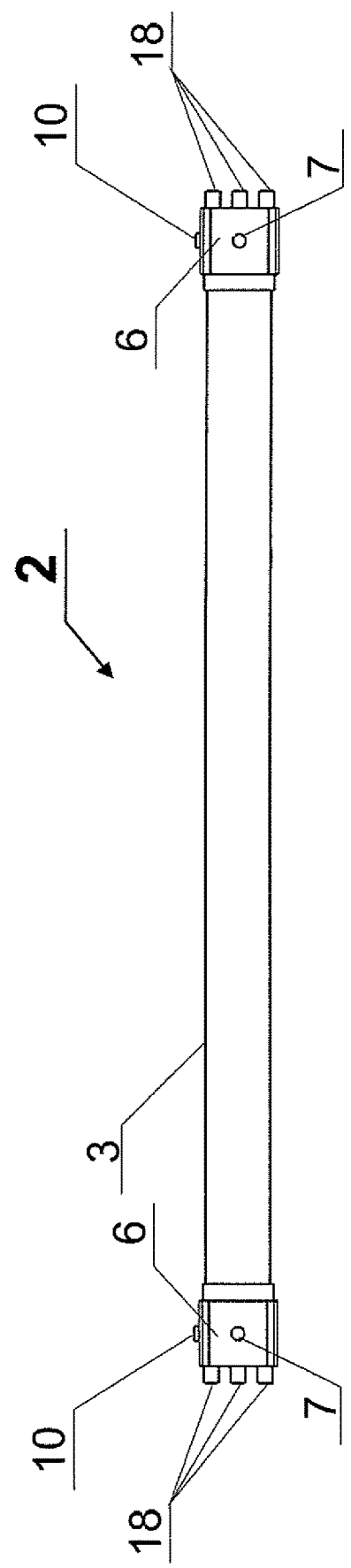
Figure 3:
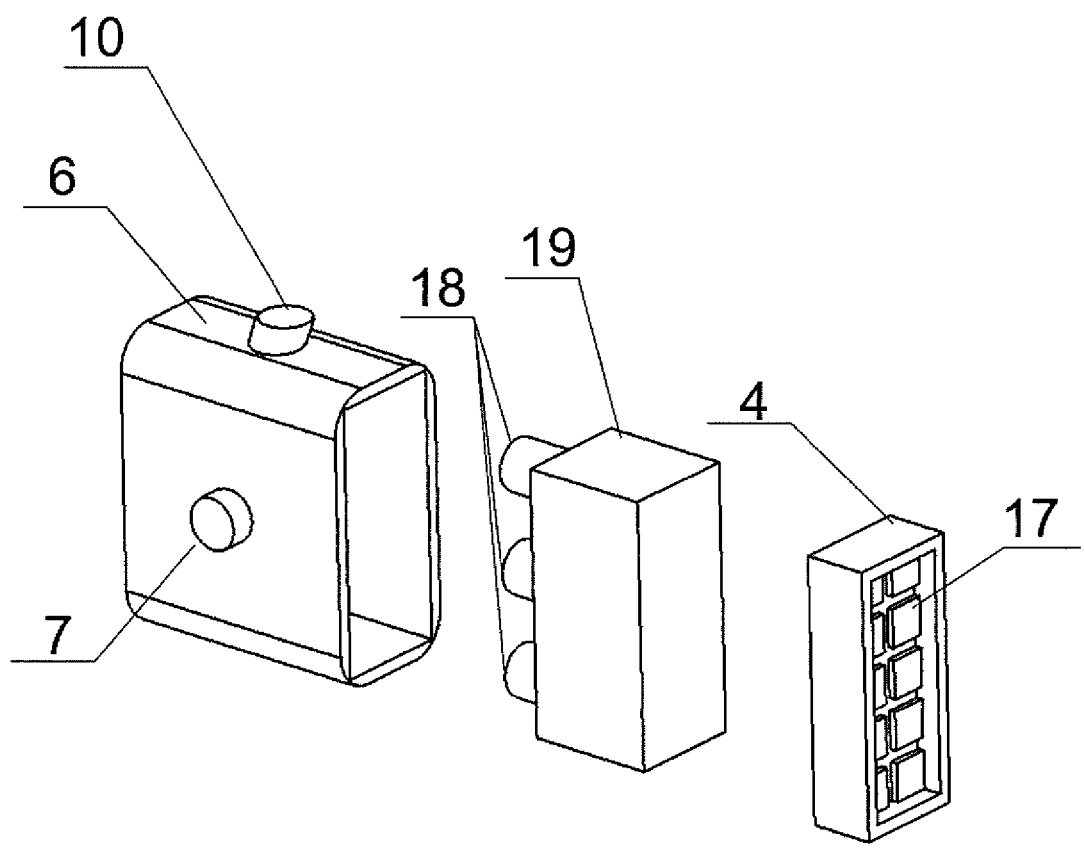
Figure 4:
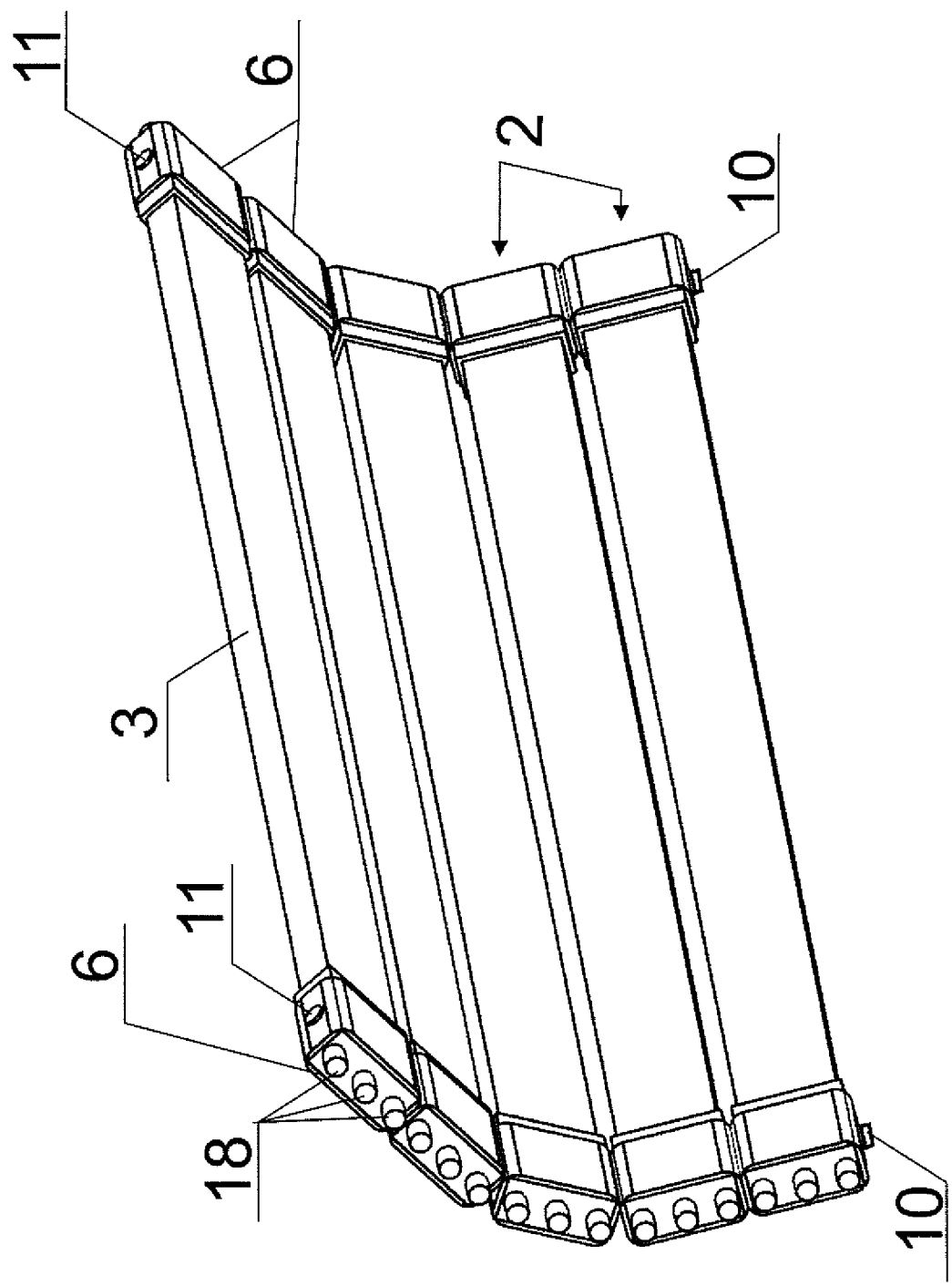
Figure 5:
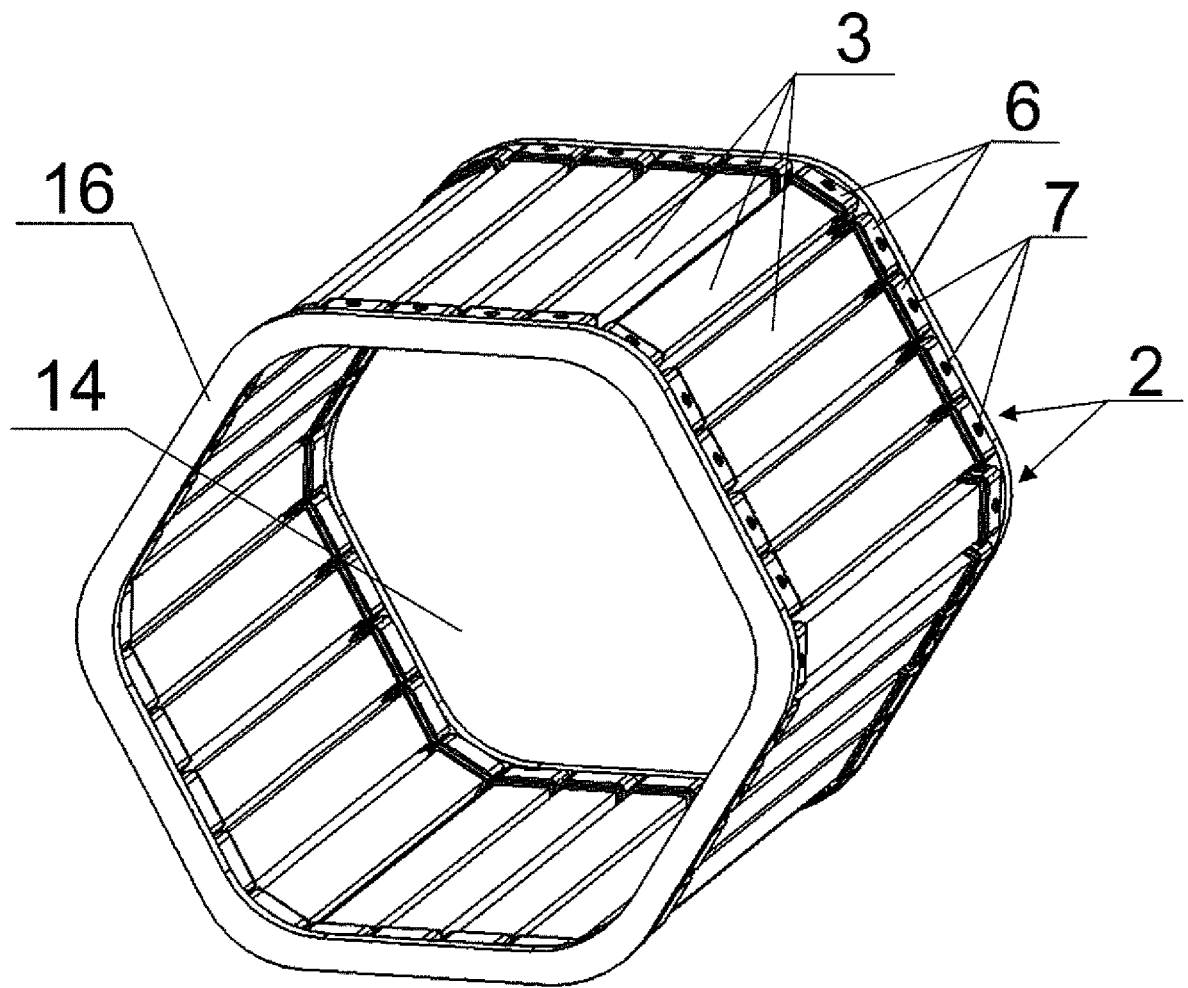
Figure 6:
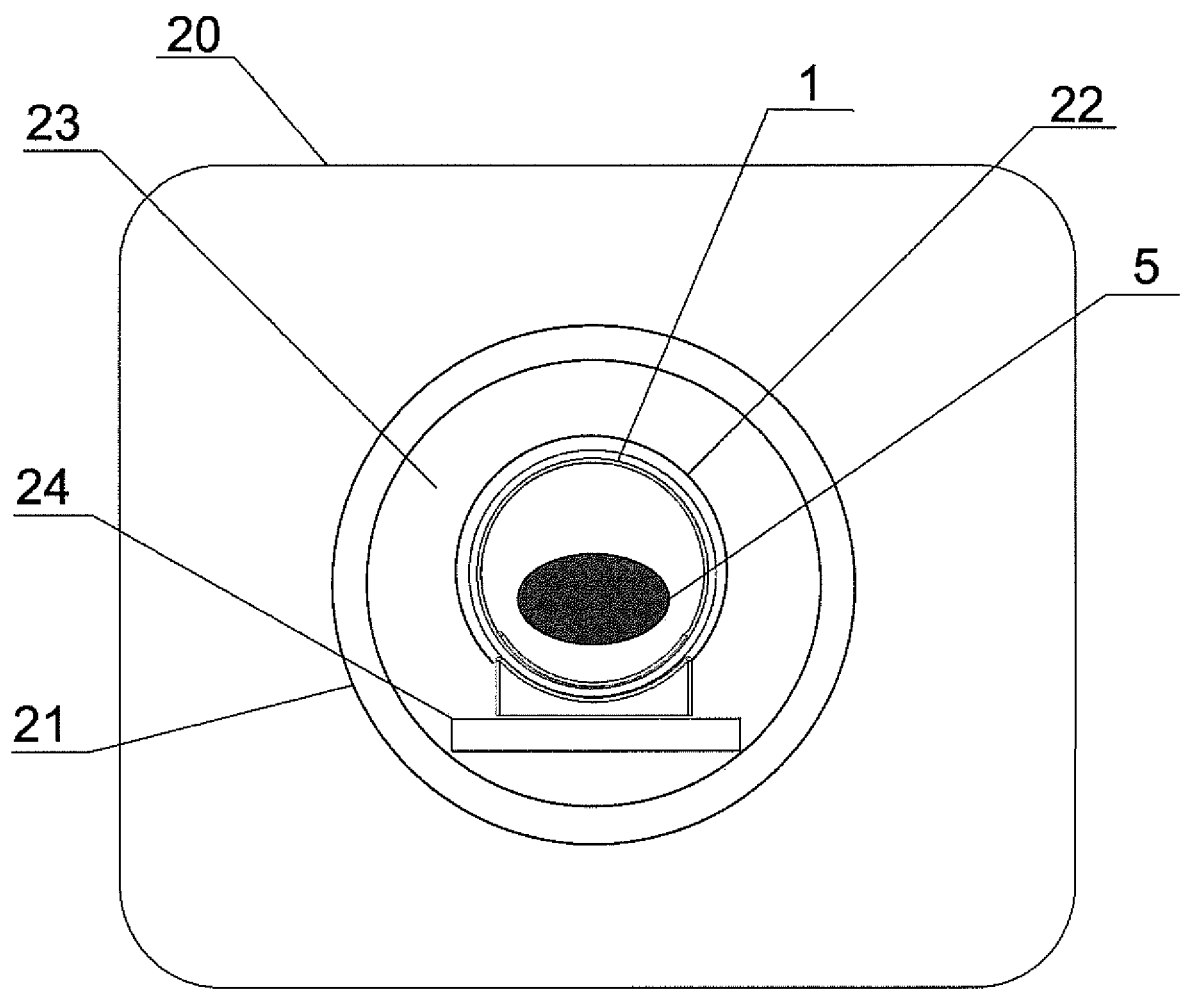
Figure 7:
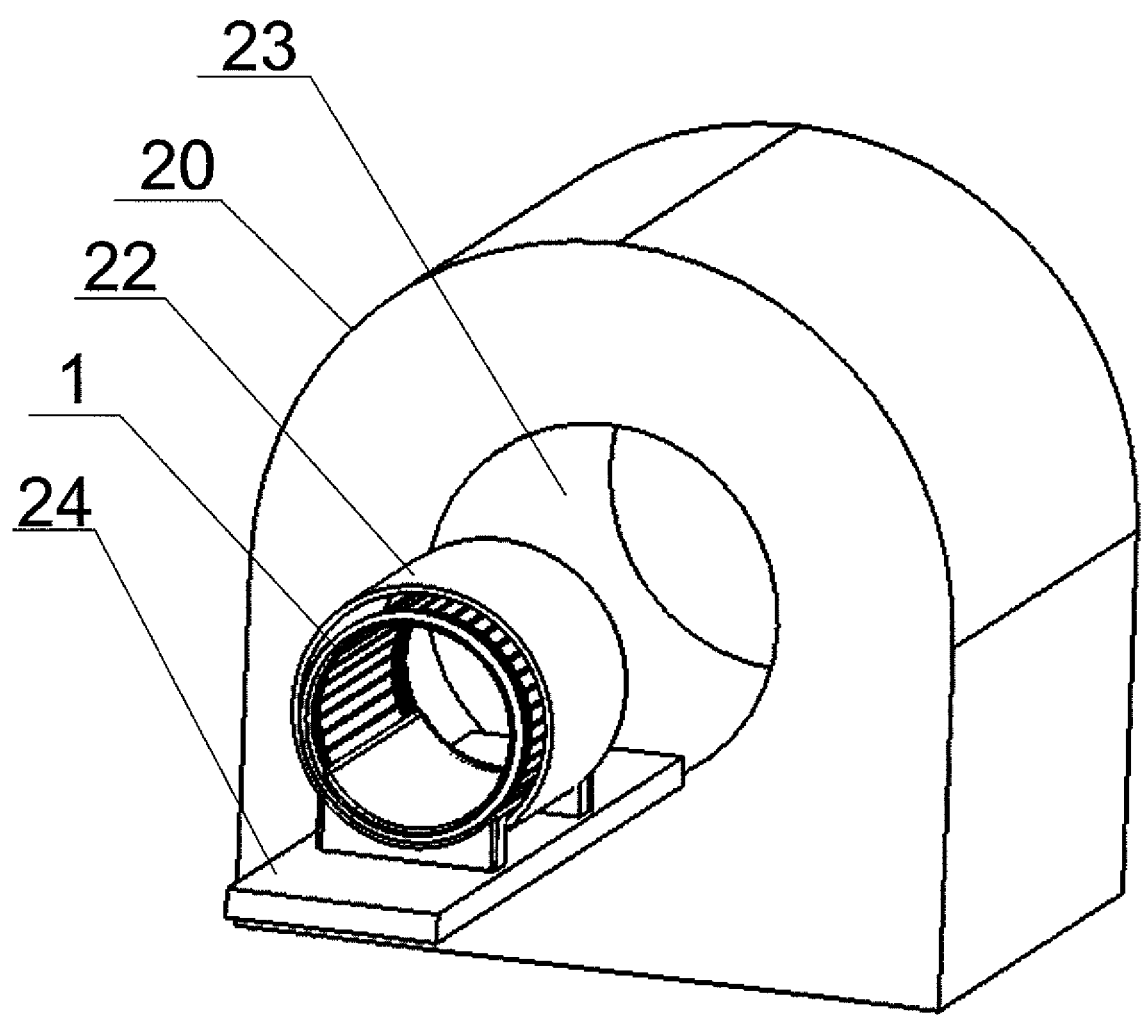

The examples of possible embodiment of the invention have been shown on the drawing, in which FIG. 1 presents schematically a front view of a TOF-PET tomography insert, FIG. 2 presents schematically a top view of a detection module, FIG. 3 presents schematically a perspective view of separated components located at the end of the detection module, FIG. 4 presents an arrangement of a few detection modules connected to each other, FIG. 5 presents the arrangement of the detection modules constituting a workspace with a shape similar to a cuboid with the hexagon base, FIG. 6 presents schematically a cross-section of the MRI scanner with the TOF-PET tomograph insert placed inside, whereas FIG. 7 presents a perspective view of the MRI scanner and the TOF-PET tomography insert which is placed inside the transmitter-receiver coil situated on the patient bed of the MRI scanner, before the bed is inserted into the diagnostic tunnel of the MRI scanner.

As shown in FIG. 4, FIG. 5 and FIG. 7 the TOF-PET tomography insert 1, according to the possible embodiment of the invention, is comprised of detection modules 2. As shown in FIG. 2 and FIG. 3 each detection module 2 comprises a scintillator stripe 3, which at both ends is connected to the photoelectric converter 4 which converts light signals from the scintillator stripe 3 into electric signals, and further with the signal processing electronic circuit 19, protected with the housing 6.

As shown in FIG. 3, in this possible embodiment of the invention, the photoelectric converters 4 constitute silicon photomultipliers 17, arranged in a two dimensional array configuration. The size and dimensions of the silicon photomultipliers 17 array is adapted to the size and dimensions of the cross-section of the plastic scintillator stripe 3. If the dimensions of the cross-section of the stripe are, for example, 5 mm by 20 mm, and the silicon photomultiplier 17 has dimensions of 5 mm by 5 mm, then four silicon photomultipliers 17 can be attached to one end of the scintillator stripe 3. Each silicon photomultiplier 17 is arranged next to another identical silicon photomultiplier 17, so they adjoin to each other with the edges. FIG. 3 shows photoelectric converter 4 composed of silicon photomultipliers 17, arranged in two columns of five silicon photomultipliers 17 in one column. It is clear that in other possible embodiments of the invention, one may use any of known photoelectric converters 4, for example, avalanche diodes, or photomultiplier tubes. Although the photoelectric converters 4 are in the magnetic field of the MRI scanner 20, the tomography TOF-PET insert does not interfere with the technical parameters of the MRI scanner 20, and does not interfere the operation of the MRI scanner 20.

Each detection module 2 is equipped with coupling elements for establishing a detachable connection of detection modules 2, located next to each other. In this possible embodiment of the invention, a coupling element constitutes a protrusion 10, located on the housing 6 of one of the detection module 2, and the groove 11, which is located on the housing 6 of adjacent detection module 2, but it is obvious that other known solutions for detection modules 2 coupling may be used. Housings 6, through the coupling elements (protrusions 10 and grooves 11), are rigidly connecting the two detection modules 2 on both sides. Coupling elements have the ability to adjust the angle at which they are connected to the next detection module 2, giving the possibility to choose the geometry of the entire TOF-PET tomography insert 1.

Detection modules 2 may be connected together in such a way that they constitute a workspace 14 of the TOF-PET insert in the form of a cylinder, as shown in FIG. 1, FIG. 6 and FIG. 7, or with a shape similar to a cuboid with the hexagon base, as shown in FIG. 5, or any other. Detection modules 2 may consist of the plastic scintillator stripe 3, of arbitrary length and cross-section shape. It is not possible to change the physical properties of already made plastic scintillator stripes 3, but geometries and sizes may be chosen during the plastic scintillator stripes 3 manufacturing process to adapt the plastic scintillator stripe 3 to the specific application or geometry of investigated object.

With the use of many stripes of different shapes, depending on the requirements, one may assemble the tomography TOF-PET insert in such a way that it will fit to a specific transmitter-receiver coil 22, such as a head coil of a specific MRI scanner 20. The variable connection angle on the coupling elements between the detection modules 2, allows for changing the configuration of the detection modules. The number of detection units 2 can be chosen to adjust the size of the TOF-PET tomography insert to actual needs: removing or adding individual detection modules 2 to the configuration. The imaged volume of the patient's body 5, depending on what structures it concerns, can be put into the interior of the TOF-PET tomography insert (head, upper/lower limb, for instance) or two halves (top and down) of the TOF-PET tomography insert may be imposed one to another surrounding the investigated volume of the patient's body 5 (chest, for example).

To strengthen the construction formed from the detection modules 2, bracket 16 may be applied, which has sockets for the outputs 18, outgoing from the signal processing electronic circuit 19 at the ends of the detection modules 2. In the possible embodiment, shown in FIG. 5, two brackets 16 were utilized on both sides of coupled detection modules 2. Brackets 16 at the same time support and protect power and signal circuits, supplied to the detection module 2 at each side. The bracket 16 has a shape adapted to the configuration of coupled detection modules 2, and, as it is shown in possible embodiment presented in FIG. 1 or FIG. 7, it has for example a form of a ring, or has a shape close to regular hexagon, as shown in possible embodiment in FIG. 5.

The detection modules 2 are entirely made of non-magnetic material and each detection module 2 is equipped at each end with a liquid marker 7. In this possible embodiment of the invention, the liquid marker 7 is an ampule with an aqueous solution of a chemical compound that shortens the longitudinal relaxation time of water. For example, the chemical compound may be $NiSO_4$ and $CuSO_4$. Liquid markers 7 give a signal in magnetic resonance imaging, and are visible in an MRI image. This allows for determination of spatial position of each detection module 2 of the TOF-PET tomography insert 1 placed inside the tunnel of the MRI scanner 20 using the magnetic resonance imaging technique.

The TOF-PET tomography insert is equipped with a liquid marker device 8, as shown in FIG. 1. In this possible embodiment of the invention, a liquid marker device 8 is located on a front face surface of the TOF-PET tomography insert 1, which is perpendicular to the plastic scintillator stripes 3, and has a form of an ampoule with an aqueous solution of a chemical compound which shortens the longitudinal relaxation time of water. For example, such a compound may be $NiSO_4$ or $CuSO_4$. Liquid marker device 8 gives the signal in magnetic resonance imaging and is visible on the MRI image. This allows for a spatial positioning of the TOF-PET tomography insert inside the MRI scanner 20, as well as establishing the relation of the geometry and dimensions of the TOF-PET tomography insert 1 and PET image with the MRI image.

The TOF-PET tomography insert 1 is equipped with electronic signal processing unit, and with a computer having software for controlling the signal processing electronics, and software for reconstruction and image preservation similarly as in any TOF-PET scanner. Signal processing electronics and a computer with the aforementioned software operate independently of the MRI measurement setup.

As shown in FIG. 1 the TOF-PET tomography insert 1 has a protective layer 13 made of non-magnetic material, for protecting the detection modules 2 from inside of the working space 14. The protective layer 13 secures scintillator stripes 3 against mechanical damage, for example by the patient 5. The protective layer 3 does not disturb imaging system performance, which consists of the TOF-PET tomography insert 1, and the MRI scanner 20.

The TOF-PET tomography insert 1 is equipped with a base 12 made of non-magnetic material, as shown in FIG. 1. The base 12 of the TOF-PET tomography insert 1 does not perturb imaging system performance, which consists of the TOF-PET tomography insert 1 and the MRI scanner 20. The base 12 provides stability to the construction formed by the coupled detection modules 2, which is placed on the sliding bed 24 of the MRI scanner 20, or when one uses the TOF-PET tomography insert outside the MRI scanner as a standalone device. The base 12 should be made of non-magnetic materials, including plastic, that has sufficient strength to support the weight up to several tens of kilograms. To the base 12, brackets 16 are mounted which support the configuration of detection modules 2 forming the TOF-PET tomography insert 1.

The TOF-PET tomography insert 1 is equipped with a triggering unit 15. It is a receiving coil, with a resonance frequency in the vicinity of the resonance frequency of hydrogen atoms nuclei (magnetic resonance pulse frequency). Starting the MRI study it generates a voltage signal in the coil of the triggering unit 15, which presence is recorded and determines the start of the PET acquisition. Triggering unit 15 starts the process of PET imaging simultaneously with the start of MRI imaging.

Using only non-magnetic components for the construction of the TOF-PET tomography insert 1 provides that the homogeneity of the MRI scanner 20 magnetic field in test volume remains unaffected. For the same reason the parameters of electromagnetic fields applied during the performance of the MRI scanner 20 do not change with respect to the performance of the MRI scanner 20 as a standalone device. The data acquisition of the TOF-PET tomography insert 1 is performed by the computer system which is independent of the MRI scanner 20. Time synchronization between the TOF-PET tomography insert 1, and MRI scanner 20 does not require an electrical connection between the devices. Spatial synchronization of the MRI and PET images does not require changes in the software of the MRI system, which functionality is usually limited by the manufacturer. Interference in the MRI system software is usually forbidden, beside the changes (to the extent permitted by the manufacturer) of basic parameters of the imaging sequences, or recording and processing of acquired images for further radiologic interpretation purposes. The synchronization is performed by the PET image reconstruction system relying on the MRI images, where signals from liquid markers 7, placed at both ends of each detection module 2, as well as from liquid marker device 8, are present.

Location of the signals from liquid markers 7 and liquid marker device 8 on the MRI images gives a possibility of imposing the PET and MRI images of the investigated object avoiding the problems related to images relative shifts in three spatial dimensions as well as with their relative dimensional scaling.

The TOF-PET tomography insert, is a TOF-PET scanner, but designed in the way that it can operate as a standalone device or within any MRI scanner 20, inside the transmitting-receiving coils 22, being an independent and non-interfering in MRI scanner 20 construction. The TOF-PET tomography insert 1 does not interfere in the technical parameters of the MRI scanner 20 and does not interfere in operation of the MRI scanner 20. MRI scanner 20 operation does not interfere with the operation of the TOF-PET tomography insert 1, and does not interfere in the technical parameters of the TOF-PET tomography insert 1. The modular design of the TOF-PET tomography insert 1 enables to arrange the geometry of the detection modules 2 according to the size and shape of the transceiver coil 21, which is built in the MRI scanner 20, in particular local transmitter-receiver coil 22, which is not an integral part of the MRI scanner 20, and is dedicated to the study of individual patient's 5 body parts (head, arm, leg, for instance) or to the geometry and dimensions of the investigated object. The latter requires to combine the appropriate number of detection modules 2 of the appropriate shape and size. This can be done even immediately prior to imaging.

The TOF-PET tomography insert 1 has an unique system for positioning inside the MRI scanner 20, as well as the triggering unit 15 to synchronize the PET and MRI acquisition timing. The TOF-PET tomography insert 1 may be put inside the MRI scanner 20 diagnostic tunnel 23 to enable simultaneous PET and MRI imaging. At the end of the combined imaging procedure, the TOF-PET tomography insert 1 may be taken out from the MRI scanner 20 diagnostic tunnel 23. These operations may be performed in a short time. The TOF-PET tomography insert 1 is a compact, lightweight device, which handling shall not constitute a problem for the operating staff. This solution is desired to be much cheaper than commercially available TOF-PET scanners.

The greatest advantage of the invention is that it may be directly used in any MRI scanner 20, which is currently held by the medical units as hospitals, so that the MRI scanner 20 and the TOF-PET tomography insert 1 introduced into the MRI scanner 20 diagnostic tunnel 23 constitute a device for the simultaneous MRI and PET imaging.

The invention is clearly not limited to the disclosed embodiments, and there are various modifications within the framework of the patent claims without departing from the essence of the invention.

The invention claimed is:

1. A Time-of-Flight Positron Emission Tomography (TOF-PET) tomography insert, comprising:
detection modules, each detection module made of a non-magnetic material and comprising a scintillator stripe;
photoelectric converters, each photoelectric converter connected to a dedicated scintillator stripe and configured to convert light signals from the scintillator stripe to electric signals;
wherein each of the photoelectric converters is connected to an electronic signal processing circuit protected by a housing and comprising an electronic signal processing unit and a computer operable to control the electronic signal processing unit and to reconstruct and store images;
wherein each of the detection modules further comprises, at each of ends of the scintillator stripe, a liquid marker visible in a magnetic resonance image;
a liquid marker device visible in the magnetic resonance image;
wherein adjacent detection modules are detachably connected via coupling elements.

2. The tomography insert according to the claim 1, wherein the adjacent detection modules are detachably connected by a groove and protrusion coupling.

3. The tomography insert according to claim 1, further comprising a protective layer made of a non-magnetic material that protects the detection modules from the inside of a working space formed by the coupled detection modules.

4. The tomography insert according to claim 1, wherein the photoelectric converters are silicon photomultipliers arranged in a two-dimensional matrix comprising at least two elements.

5. The tomography insert according to claim 1, wherein the liquid marker device is located on a front face of the tomography insert, the front face being perpendicular to the scintillator stripes.

6. The tomography insert according to claim 1, wherein the liquid marker device is an ampoule comprising an aqueous solution of a chemical compound that shortens a longitudinal relaxation time of water.

7. The tomography insert according to claim 1, Wherein the liquid markers have a form of ampoules with an aqueous solution of a chemical compound that shortens a longitudinal relaxation time of water.

8. The tomography insert according to claim 1, further comprising at least one bracket.

9. The tomography insert according to claim 8, wherein the bracket has an output slot for the electronic signal processing circuit placed at an end of each detection module.

10. The tomography insert according to claim 1, further comprising a support base made of a non-magnetic material.

11. The tomography insert according to claim 1, comprising a bracket attached to a support base.

* * * * *